United States Patent [19]

Suh et al.

[11] 4,347,246
[45] Aug. 31, 1982

[54] ANTIHYPERTENSIVE LACTAMS

[75] Inventors: John T. Suh, Greenwich, Conn.; Bruce E. Williams, Cottage Grove, Minn.; Jerry W. Skiles, Tuckahoe; Bernard Loev, Scarsdale, both of N.Y.

[73] Assignee: USV Pharmaceutical Corporation, Tuckahoe, N.Y.

[21] Appl. No.: 263,824

[22] Filed: May 15, 1980

Related U.S. Application Data

[63] Continuation-in-part of Ser. No. 142,945, Apr. 23, 1980, Pat. No. 4,287,203.

[51] Int. Cl.³ ............... A61K 31/55; C07D 281/04; C07D 281/18
[52] U.S. Cl. ..................... 424/246; 260/239.3 B; 260/239.3 R; 260/239.3 T; 260/239.3 P; 424/248.51; 424/258; 424/267; 424/274; 424/275; 424/273 B; 424/270; 424/263; 424/273 R
[58] Field of Search ............... 260/239.3 B; 424/275, 424/246, 248.51, 258, 263, 273 R, 274, 273 B

[56] References Cited

U.S. PATENT DOCUMENTS 3,562,257  2/1971  Kugita et al. .......... 260/239.3 B

Primary Examiner—Robert T. Bond

[57] ABSTRACT

A compound of the formula

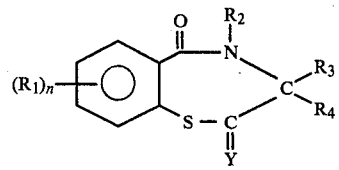

wherein:
$R_1$ is independently lower alkyl having from 1 to 6 carbon atoms, lower alkenyl having from 2 to 6 carbon atoms, lower alkynyl having from 2 to 6 carbon atoms, hydroxy, hydroxyalkyl, alkoxy, thio, thioalkyl, alkylmercapto, amino, aminoalkyl, alkylamino, nitro, cyano, alkanoyl, carboxy, carboxyalkyl, carbalkoxy, carbalkoxyalkyl, halogen, alkylsulfoxy, alkylsulfonyl, sulfonyl, sulfonamido, trifluoromethyl, or methylenedioxy, wherein the alkyl group in hydroxyalkyl, thioalkyl, aminoalkyl, carboxyalkyl, alkoxy, alkylmercapto, alkylsulfoxy, alkanoyl, carbalkoxy, and carbalkoxyalkyl has from 1 to 6 carbon atoms, n is an integer from 1 to 4 inclusive, $R_2$ is selected from the group consisting of hydrogen and cycloalkyl, wherein the cycloalkyl group contains from 3 to 16 carbon atoms, $R_3$ and $R_4$ are hydrogen, and Y is oxygen, sulphur, $=NR_1$, $=NOR_1$ or $=N-NH_2$, $R_1$ being the same as defined above.

The compounds are useful as antihypertensives, and have angiotensin converting enzyme inhibitory activity.

9 Claims, No Drawings

ANTIHYPERTENSIVE LACTAMS

This application is a continuation-in-part of patent application Ser. No. 142,945, filed Apr. 23, 1980, now U.S. Pat. No. 4,287,203, issued Sep. 1, 1981.

This invention relates to new chemical compounds possessing valuable pharmaceutical activity. It particularly relates to compounds possessing antihypertensive and angiotensin converting enzyme inhibitory activity and having the structure:

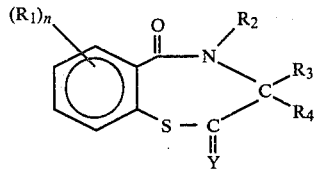

wherein
R$_1$ is independently alkyl, alkenyl, alkynyl, hydroxy, alkoxy, hydroxyalkyl, thio, thioalkyl, alkylmercapto, amino, aminoalkyl, alkylamino, nitro, cyano, alkanoyl, carboxy, carboxyalkyl, carbalkoxy, carbalkoxyalkyl, halogen, trifluoromethyl, methylenedioxy, alkylsulfoxy, alkylsulfonyl, sulfonyl, or sulfonamido, n is an integer from 1 to 4 inclusive, R$_2$, R$_3$ and R$_4$ are independently hydrogen, alkyl, alkenyl, alkynyl, cycloalkyl, cycloalkyl-alkyl, polycycloalkyl, polycycloalkylalkyl, aryl, aralkyl, heteroaryl, heteroarylalkyl, heterocycloalkyl, heterocycloalkyl-alkyl, fused arylcycloalkyl, fused arylcycloalkyl-alkyl, fused heteroarylcycloalkyl, fused heteroarylcycloalkyl-alkyl, substituted alkyl such as hydroxyalkyl, carboxyalkyl, carbalkoxyalkyl, alkoxyalkyl, alkylthioalkyl, alkylaminoalkyl, or dialkylaminoalkyl, and Y is =O, =S, =NR$_1$, =NOR$_1$, or =N-NH$_2$, R$_1$ being the same as defined above.

The alkyl groups per se and in the alkyl moiety in aralkyl, cycloalkyl-alkyl, polycycloalkyl-alkyl, heteroaryl-alkyl and the like, and, in alkoxy, alkylthio, alkanoyl, carbalkoxy, and alkylamino, may be straight chained or branched and contain from 1 to 20 carbons. Preferably, they are lower alkyl groups containing from 1 to 6 carbon atoms. Such groups include methyl, ethyl, propyl, isopropyl, butyl, isobutyl, amyl, iso-amyl, hexyl, and the like.

The alkenyl and alkynyl groups may also be branched or straight-chained and contain from 2 to 20 carbon atoms. Preferably, they contain from 2 to 6 carbon atoms. Such groups include vinyl, ethynyl, propenyl, allyl, isopropenyl, and the like.

The cycloalkyl, polycycloalkyl, aryl, heteroaryl, aryalkyl, fused aryl-cycloalkyl groups and the like contain from 3 to 16 carbon atoms and may carry substituents such as lower alkyl, alkenyl, alkynyl, hydroxy, thio, amino, alkoxy, alkylthio, alkyl-amino, sulfonyl, sulfonamido and halo. They include such radicals as cyclopropyl, cyclobutyl, cyclopentyl, cyclohexyl, cycloheptyl, adamantyl, norbornyl, phenyl, tolyl, benzyl, phenethyl, dimethoxyphenyl, hydroxybenzyl, indanyl, naphthyl, tetrahydronaphthyl, decahydronaphthyl, pyridyl, quinolyl, pyrrolidyl, pyrrolyl, morpholinyl, furyl, furfuryl, tetrahydrofurfuryl, benzimidazolyl, thiomorpholinyl, thienyl, imidazolyl, tetrahydroindolyl, and the like.

The alkylene groups may be branched or straight-chained and contain from 1 to 20 carbon atoms, preferably 1 to 6 carbon atoms. Such groups include methylene, ethylene, propylene, butylene, 1-methyl propylene, 2-ethylbutylene, and the like.

The alkenylene and alkynylene groups may also be branched or straight-chained and contain from 2 to 16 carbon atoms, preferably 2 to 6 carbon atoms.

Compounds of the present invention may be prepared by cyclizing an appropriately substituted amide of the structure

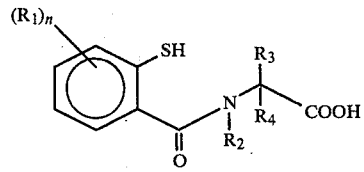

in the presence of triethylamine and ethyl chloroformate to give the desired structure where Y is =O, where Y is =O or one of the other radicals the desired compound may be obtained by replacing the —COOH with

or where Y is as described.

The preparaton of certain starting materials is also described in U.S. patent application Ser. No. 057,175 now U.S. Pat. No. 4,256,761.

In the above scheme of preparation R$_1$, R$_2$, R$_3$, R$_4$, Y and n are as previously defined.

It is known to those skilled in the art that those compounds of the present invention having asymmetric carbon atoms may exist in racemic or optically active forms. All of these forms are contemplated within the scope of the invention.

The invention will be more fully illustrated in the examples which follow. These examples are given by way of illustration and are not considered as limiting.

EXAMPLE 1

A. 3-Chloro-2-aminobenzoic acid

Sodium dithionite (104.4 g, 0.6 m) in water (400 ml) was added in portions to a slurry of 3-chloro-2-nitrobenzoic acid (30 g, 0.15 m) in water (200 ml) containing concentrated ammonium hydroxide solution (10 ml). After stirring an additional 20 minutes the mixture was filtered, acidified to pH 3-4 with concentrated hydrochloric acid and filtered again. The filtrate was saturated with sodium chloride and extracted with ether. Drying and concentration of the extract gave a white powder which was combined with the precipitates above. The crude product was used without further purification.

B. Di(2-Chloro-6-carboxyphenyl)disulfide

Sodium nitrite (6.9 g, 0.10 m) in water (30 ml) at 0° C. was added in one portion to a slurry of 3-chloro-2-aminobenzoic acid (17.2 g, 0.10 m) in concentrated hydrochloric acid (20 ml) water (50 ml) containing crushed ice. The mixture was shaken vigorously for several minutes, then filtered. The cold filtrate was slowly added at 0° C. to a solution of sodium sulfide nonahydrate (26 g, 0.11 m), sulfur (3.4 g, 0.11 m), sodium hydroxide (4.0 g, 0.10 m) and water (40 ml). The mixture was brought to room temperature over several hours, filtered and acidified (concentrated hydrochloric acid) and the disulfide collected by filtration.

C. 3-Chloro-2-mercaptobenzoic acid

Di(2-Chloro-6-carboxyphenyl)disulfide (13.4 g, 35.7 mmol), zinc (7.5 g, 115 mmol) and glacial acetic acid (150 ml) were refluxed one hour; more zinc (7.5 g, 115 mmol) was added, and reflux was continued an additional 3 hours. The mixture was cooled and filtered and the precipitate extracted with hot dilute sodium hydroxide solution. Acidification of the extract (concentrated hydrochloric acid) gave the solid product.

D. 2-Acetylthio-3-chlorobenzoic acid

3-Chloro-2-mercaptobenzoic acid (9.8 g, 52 mmol), acetic anhydride (6.3 g, 62 mmol) and glacial acetic acid (22 ml) were heated at 80° C. for 4 hours, then cooled and mixed with dilute hydrochloric acid.

The crystalline product was filtered.

E. N-(2-Acetylthio-3-chlorobenzoyl)-N-cyclopentylglycine t-butyl ester

2-Acetylthio-3-chlorobenzoic acid (11.5 g, 50 mmol) and N-cyclopentylglycine t-butyl ester (10.0 g, 50 mmol) in methylene chloride (350 ml) were cooled to 0°–5° C., and N,N$^1$-dicyclohexylcarbodiimide (10.3 g, 50 mmol) in methylene chloride (50 ml) was added. The mixture was stirred overnight. The DCC-urea was filtered and washed with $CH_2Cl_2$. The filtrate was then washed 2×125 ml 1N HCl, 2×125 ml saturated NaHCO$_3$, 2×125 ml brine, dried (MgSO$_4$), filtered and concentrated to give 20.6 g of an oil. The crude product was used without further purification in the next step.

F. N-(2-Thioacetyl-3-chlorobenzoyl)-N-cyclopentylglycine

N-(2-Thioacetyl-3-chlorobenzoyl)-N-cyclopentylglycine t-butyl ester (20.6 g, 0.05 mol) was dissolved in 150 ml $CH_3CN$. Sodium iodide (11.3 g, 0.075 m) was then added. The resulting slurry was covered with nitrogen and warmed to 55° C. Chlorotrimethylsilane (8.15 g, 0.075 m) was then added in one portion. The reaction was stirred 30 minutes at 55° C. under nitrogen atmosphere. The heat source was removed and the reaction cooled to room temperature in an ice bath. Water (60 ml) and $CH_2Cl_2$ (100 ml) were then added. The aqueous layer was quickly withdrawn and the organic layer washed 2×75 ml H$_2$O, 2×75 ml Na$_2$S$_2$O$_3$ and 2×75 ml brine. The organic layer was then dried (MgSO$_4$), filtered and concentrated to yield a dark yellow oil.

The oil was dissolved in saturated NaHCO$_3$. The alkaline solution was washed 3×100 ml ethyl acetate. The organic extracts were discarded and the alkaline solution acidified with concentrated HCl. The acidic solution was washed 4×200 ml $CH_2Cl_2$, the organic extracts combined, dried (MgSO$_4$), filtered and concentrated to yield 11.2 g (0.032 mol) of an oil which did not crystallize.

Further purification was done using a 12″×1½″ silica gel column and eluting with hexane:ethylacetate:acetic acid (5:5:0.3). This afforded 7.4 g of a glassy material. On repeated washing with refluxing hexane this provided an amorphous solid.

G. N-(2-Mercapto-3-chlorobenzoyl)-N-cyclopentylglycine

To a chilled solution of methanolic ammonia (50 ml) was added 3.7 g (0.0104 m) of N-(2-thioacetyl-3-chlorobenzoyl)-N-cyclopentylglycine. The reaction was covered with nitrogen and stirred 3 hours while warming slowly from 0° C. to room temperature.

The clear, yellow solution was concentrated in vacuo. The crude material was dissolved in ethyl acetate and washed 2×50 ml 1N HCl, 2×50 ml brine, dried (MgSO$_4$), filtered and concentrated to yield 3.0 g (0.0095 m) of an oil which later solidified. This material was recrystallized from hexane:ethyl acetate (1:1), m.p. 141°–142° C.

H. 9-Chloro-4-cyclopentyl-1,4-benzothiazepine-2,5(3H) dione

In a round-bottom flask 5.5 g (0.0175 m) of the thiol-acid and 1.8 g (0.0175 m) of triethylamine were combined in 100 ml $CH_2Cl_2$. The solution was cooled in an ice bath to 0° C. Ethyl chloroformate (1.9 g, 0.0175 m) in 10 ml $CH_2Cl_2$ was added slowly dropwise to the chilled solution. The reaction was then stirred 30 minutes at 0° C. and 2 hours at room temperature.

At the end of this period, the reaction was washed 2×75 ml dil HCl and 2×75 ml brine. The organic layer was dried (MgSO$_4$) and concentrated to a yellow oil. The oil was purified by HPLC using hexane:ethyl acetate (1:1) as the solvent system. This chromatography produced 1.5 g (30%) of white crystals which were recrystallized from hexane:ethyl acetate. M.P. 117°–118° C.

EXAMPLE 2

A. 2-Amino-3-methoxybenzoic acid

Sodium dithionite (84 g, 0.48 m) in water (100 ml) was added to 2-nitro-3-methoxybenzoic acid (20 g, 0.10 m) in water (100 ml)/concentrated ammonium hydroxide solution (6 ml). After stirring 3 hours the product was filtered. Acidification of the filtrate, saturation with sodium chloride and extraction with ether provided a small second crop of product.

B. 2-Mercapto-3-methoxybenzoic acid

A slurry of 2-amino-3-methoxybenzoic acid (22.3 g, 0.133 m) in water (66 ml)/concentrated hydrochloric acid (27 ml) was diazotized at 0° C. with sodium nitrite (9.3 g, 0.135 m) in water (37 ml). The supernatant liquid was decanted from insoluble matter and added at 0° C. to a mixture of sulfur (4.5 g, 0.14 m), sodium sulfide nonahydrate (34.7 g, 0.144 m) and sodium hydroxide (5.2 g, 0.13 m) in water (47 ml). After two days the mixture was filtered and acidified to yield the solid disulfide.

The moist product, zinc (10 g, 0.15 m) and glacial acetic acid (200 ml) were refluxed 1 hour, a second portion of zinc (10 g, 0.15 m) was added and reflux was continued for 3 hours. After cooling, the precipitate was filtered and extracted with dilute sodium hydroxide solution. The basic extract was acidified and the solid product collected.

C. 2-Acetylthio-3-methoxybenzoic acid

A solution of 2-mercapto-3-methoxybenzoic acid (14.6 g. 79 mmol), acetic anhydride (9.7 g. 95 mmol) and glacial acetic acid (35 ml) was refluxed 15 minutes, then cooled and poured into dilute hydrochloric acid.

D. N-(2-Acetylthio-3-methoxybenzoyl)-N-cyclopentylglycine

N,N'-Dicyclohexylcarbodiimide (10.3 g, 50 mmol) in methylene chloride (80 ml) was added to 2-acetylthio-3-methoxybenzoic acid (11.3 g, 50 mmol) and N-cyclopentylglycine t-butyl ester (10.0 g, 50 mmol) in methylene chloride (300 ml) at 0°-5° C. Overnight stirring was followed by filtration and washing of the filtrate with dilute hydrochloric acid, sodium bicarbonate solution and brine. Dryng and concentration gave a gum which was dissolved in acetonitrile (65 ml), combined with sodium iodide (11.2 g, 75 mmol) and heated to 40°-50° C. Chlorotrimethylsilane (8.1 g, 75 mmol) was introduced and the mixture was heated for 30 minutes, then quenched with water. The organic phase was washed with water, aqueous sodium thiosulfate and brine then concentrated. Aqueous sodium bicarbonate was added to the residue and the resulting solution was washed with methylene chloride and ether, then acidified and extracted with ethyl acetate. The organic portion was dried and concentrated and the residue passed through a silica gel column to provide the amorphous product.

E. N-(2-Mercapto-3-methoxybenzoyl)-N-cyclopentylglycine

N-(2-Acetylthio-3-methoxybenzoyl)-N-cyclopentylglycine (4.4 g, 12.5 mmol) was stirred with excess sodium hydroxide solution for 2 hours at 25° C., then acidified and extracted with ethyl acetate. The extract was washed with water and brine, then dried and concentrated. The amorphous product was obtained by column chromatography of the residue.

F. 4-Cyclopentyl-9-methoxy-1,4-benzothiazepine-2,5(3H)-dione

N-(2-mercapto-3-methoxybenzoyl)-N-cyclopentylglycine (14.5 g, 0.0469 m) and triethylamine (4.7 g, 0.0469 m) in methylene chloride (500 ml) were cooled to 0° C., and ethyl chloroformate (5.1 g, 0.0469 m) was added over one minute. The mixture was stirred 2 hours at 0°-10° C., washed (water, then brine), dried (Na2SO4) and concentrated. HPLC purification using hexane/ethyl acetate (1/1) as eluent gave the desired product. Recrystallization from ethyl acetate provided 5.4 g analytically pure material (yield: 35%).

Following the procedures of the above examples, the following additional compounds were prepared:

4-Cyclopentyl-9-methyl-1,4-benzothiazepine-2,5(3H)-dione
4-Cyclopentyl-9-trifluoromethyl-1,4-benzothiazepine-2,5(3H)-dione
4-Cyclopentyl-9-fluoro-1,4-benzothiazepine-2,5(3H)-dione
4-Cyclopentyl-8-methylsulfoxyl-1,4-benzothiazepine-2,5(3H)-dione
4-Cyclopentyl-8-methylsulfonyl-1,4-benzothiazepine-2,5(3H)-dione
4-Cyclopentyl-7-sulfamyl-1,4-benzothiazepine-2,5(3H)-dione
4-Cyclopentyl-7,9-dichloro-1,4-benzothiazepine-2,5(3H)-dione
4-(p-Tolyl)-1,4-benzothiazepine-2,5(3H)-dione
4-Cyclopentyl-9-(2-propyl)-1,4-benzothiazepine-2,5(3H)-dione
4-Cyclopentyl-9-nitro-1,4-benzothiazepine-2,5-(3H)-dione
9-Amino-4-cyclopentyl-1,4-benzothiazepine-2,5-(3H-dione
4-Cyclopentyl-8-dimethylamino-1,4-benzothiazepine-2,5-(3H)-dione
7-Carboxy-4-cyclopentyl-1,4-benzothiazepine-2,5(3H)-dione
8-Chloro-4-cyclopentyl-7-sulfamyl-1,4-benzothiazepine-2,5-(3H)-dione The compounds of the present invention have demonstrated potent activity (of the order I50 of 0.0075 to 0.05 micromols) in inhibiting the angiotensin converting enzyme (ACEI activity) when tested by the method described in Science 196, 441–4 (1977). As such, these compounds would be very useful in the treatment of hypertension. Administration of the compounds to hypertensive rats at dosages of about 100 mg/kg i.p. decreases the blood pressure by about 25 to 35% for periods of about 10-13 hours. The compounds may be administered orally or parenterally in the treatment of hypertension and it will be within the skill of the practitioner to determine the exact amount to be administered and the mode of administration.

We claim:

1. A compound of the formula

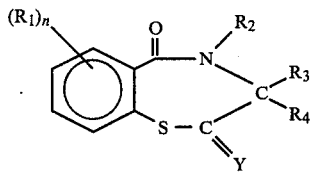

wherein $R_1$ is independently $C_1$–$C_{20}$ alkyl, $C_2$–$C_{20}$ alkenyl, $C_2$–$C_{20}$ alkynyl, hydroxy, $C_1$–$C_{10}$ alkoxy, hydroxy $C_1$–$C_{20}$ alkyl, thio, thio $C_1$–$C_{20}$ alkyl, $C_1$–$C_{20}$ amino, amino $C_1$–$C_{20}$ alkyl, $C_1$–$C_{20}$ alkylamino, nitro, cyano, $C_1$–$C_{20}$ alkanoyl, carboxy, carboxy $C_1$–$C_{20}$ alkyl, carb $C_1$–$C_{10}$ alkoxy, carb $C_1$–$C_{10}$ alkoxy, carb $C_1$–$C_{10}$ alkoxy $C_1$–$C_{20}$ alkyl, $C_1$–$C_{20}$ alkylsulfoxy, $C_1$–$C_{20}$ alkylsulfonyl, sulfonyl, sulfonamido, halogen, trifluoromethyl, or methylenedioxy, n is an integer from 1 to 4 inclusive, $R_2$, $R_3$ and $R_4$ are independently hydrogen, $C_1$–$C_{20}$ alkyl, $C_2$–$C_{20}$ alkenyl, $C_2$–$C_{20}$ alkynyl, $C_3$–$C_{16}$ cycloalkyl, phenyl, tolyl, benzyl, phenyethyl, dimethoxyphenol, hydroxybenzyl, indanyl, naphthyl, tetrahydronaphthyl, decahydronaphthyl, pyridyl, quinolyn, pyrrolidyl, pyrrolyl, morpholinyl, furyl, furfuryl, tetrahydrofurfuryl, benzimidazolyl, thiomorpholinyl, thienyl, imidazolyl, or tetrahydroindolyl, and Y is=O,=S,=NR1, =NOR1, or =N—NH2, R1 being the same as defined above.

2. A compound of the formula

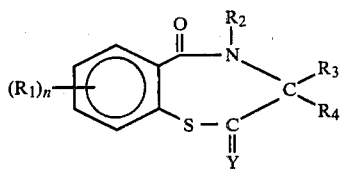

wherein:

$R_1$ is independently lower alkyl having from 1 to 6 carbon atoms, lower alkenyl having from 2 to 6 carbon atoms, lower alkynyl having from 2 to 6 carbon atoms, hydroxy, hydroxyalkyl, alkoxy, thio, thioalkyl, alkylmercapto, amino, aminoalkyl, alkylamino, nitro, cyano, alkanoyl, carboxy, carboxyalkyl, carbalkoxy, carbalkoxyalkyl, halogen, alkylsulfoxy, alkylsulfonyl, sulfonyl, sulfonamido, trifluoromethyl, or methylenedioxy, wherein the alkyl group in hydroxyalkyl, thioalkyl, aminoalkyl alkylamino, alkylsulfonyl, carboxyalkyl, alkoxy, alkylmercapto, alkylsulfoxy, alkanoyl, carbalkoxy, and carbalkoxyalkyl has from 1 to 6 carbon atoms, n is an integer from 1 to 4 inclusive, $R_2$ is selected from the group consisting of hydrogen and cycloalkyl, wherein the cycloalkyl group contains from 3 to 16 carbon atoms, $R_3$ and $R_4$ are hydrogen, and Y is oxygen.

3. A compound according to claim 2 wherein n is 1 and $R_1$ is in the 9 position.

4. A compound according to claim 3 wherein $R_2$ is cyclopentyl.

5. A compound according to claim 4 wherein $R_1$ is chloro.

6. A compound according to claim 4 wherein $R_1$ is lower alkoxy.

7. A compound according to claim 6 wherein $R_1$ is methoxy.

8. A compound according to claim 4 wherein $R_1$ is trifluoromethyl.

9. A process for treating hypertension which comprises administering to the hypertensive animal an effective amount of a compound according to claim 1.

* * * * *

UNITED STATES PATENT AND TRADEMARK OFFICE
CERTIFICATE OF CORRECTION

PATENT NO. : 4,347,246

DATED : August 31, 1982

INVENTOR(S) : John T. Suh, Bruce E. Williams, Jerry W. Skiles, and Bernard Loev

It is certified that error appears in the above-identified patent and that said Letters Patent is hereby corrected as shown below:

FRONT PAGE, left-hand column, line [22], after "Filed:", the date "May 15, 1980" should be --May 15, 1981--.

Signed and Sealed this

Twenty-fourth Day of December 1985

[SEAL]

Attest:

DONALD J. QUIGG

Attesting Officer

Commissioner of Patents and Trademarks